US00PP19955P2

(12) United States Plant Patent
LaBonte et al.

(10) Patent No.: US PP19,955 P2
(45) Date of Patent: Apr. 28, 2009

(54) SWEETPOTATO PLANT NAMED 'MURASAKI-29'

(50) Latin Name: *Ipomoea batatas*
Varietal Denomination: Murasaki-29

(75) Inventors: Don R. LaBonte, Baton Rouge, LA (US); Arthur Q. Villordon, Monroe, LA (US); Christopher A. Clark, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 11/975,203

(22) Filed: Oct. 18, 2007

(51) Int. Cl.
*A01H 5/00* (2006.01)

(52) U.S. Cl. ..... Plt./258

(58) Field of Classification Search ..... Plt./258
See application file for complete search history.

*Primary Examiner*—Annette H Para
(74) *Attorney, Agent, or Firm*—John H. Runnels; James C. Carver

(57) ABSTRACT

A new variety of sweetpotato identified as 'Murasaki-29' is disclosed having disease resistance to southern root-knot nematode and soil rot, a white flesh, and purple skin.

4 Drawing Sheets

BACKGROUND OF THE INVENTION

This invention pertains to a new and distinct variety of sweetpotato.

Sweetpotatoes, unlike Irish potatoes (*Solanum tuberosum*), are not tuber-propagated plants. A "tuber" is a short, thickened portion of an underground branch. Along a tuber "eyes" are found, each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and are not derived from an underground branch. Sweetpotatoes do not form tubers.

SUMMARY OF THE INVENTION

Genus and Species Name

This new and distinct specialty sweetpotato variety, *Ipomoea batatas* (L.) Lam. exhibited a white flesh and deep purple skin in contrast to a brown skin, white flesh mutation of 'Beauregard' named 'O'Henry' or to a white flesh, brown-skinned 'Kotobuki'. This new sweetpotato variety demonstrated superior disease resistance to southern root-knot nematode in contrast to both 'O'Henry' and 'Kotobuki' varieties, both of which are susceptible to southern root-knot nematode. This new variety also demonstrated a resistance to soil rot and fusarium root rot, similar to 'Beauregard'.

Variety Denomination

This new and distinct sweetpotato variety is identified as 'Murasaki-29', and is characterized by its white flesh, high dry matter, purple skin, and elliptical roots.

BRIEF DESCRIPTION OF THE DRAWINGS

The file of this patent contains at least one photograph executed in color. Copies of this patent or patent application with color drawing(s) will be provided by the Patent and Trademark Office upon request and payment of the necessary fee.

DETAILED BOTANICAL DESCRIPTION

This new variety of sweetpotato, named 'Murasaki-29', resulted from an open-pollinated cross to the Louisiana Agricultural Experiment Station female parent 'L89-72.' The male parent was unknown. Two patented male parents ('Bienville' U.S. Plant Pat. No. 15,380 P3 and 'L96-117' U.S. Plant Pat. No. 15,038 P2) and a patent-pending male parent ('Evangeline' U.S. application Ser. No. 11/789,681) were amount potential pollen sources in the crossing nursery. 'Murasaki-29' was developed by the Louisiana Agricultural Experiment Station to provide a specialty-type, white-flesh variety as an alternative to orange flesh, dessert types like 'Beauregard' (unpatented). 'Murasaki-29' and 'Beauregard' reacted similarly to most diseases except that 'Murasaki-29' had better resistance to southern root-knot nematode than 'Beauregard.' Specialty white-flesh varieties like 'O'Henry' (unpatented white flesh mutation of 'Beauregard') or 'Kotobuki' (unpatented) did not have resistance to southern root-knot nematode. In addition, neither 'O'Henry' nor 'Kotobuki' had dark purple skin, but instead had brown-toned skin. The female parent, 'L89-72,' had similar disease resistant characteristics to that of 'Murasaki-29,' except that 'L89-72' lacked resistance to southern root-knot nematodes.

Plants of 'Murasaki-29' exhibited light green leaves [7.5 G (green) Y (yellow) 5/6], while 'L 89-72' exhibited dark green leaves [7.5 G (green) Y (yellow) (4/4)]. Leaves of 'L 89-72' were reniform with an obtuse or emarginate leaf apex and cordate leaf base; 'Murasaki-29' had a cordate leaf with an acute apex and cordate leaf base. Color terminology used herein is in accordance with the Munsell® Book of Color (Munsell Color, GretagMacbeth LLC, 617 Little Britain Road, New Windsor, N.Y. 12553-6148). The color descriptions and color illustrations were as nearly true as reasonably possible. However, it is understood that both color and other phenotypic expressions described herein may vary from plant to plant with differences in growth, environment, and cultural conditions, without any change in the genotype of the variety 'Murasaki-29.'

'Murasaki-29' roots were stored during the winter at the Louisiana Agricultural Experiment Station (Sweetpotato Research Station) in Chase, La. 'Murasaki-29' was planted the following spring, resulting in approximately 8–10 sprouts per root. Cuttings from the sprouts were transplanted successfully for asexual reproduction. Asexual propagation of the new cultivar by cuttings has shown that the unique features of this new sweetpotato variety were stable, and that the plants reproduced true to type in successive generations of asexual propagation. Plants described herein were approximately 90–110 days in age from planting in full sun field plantings.

Figure 1:
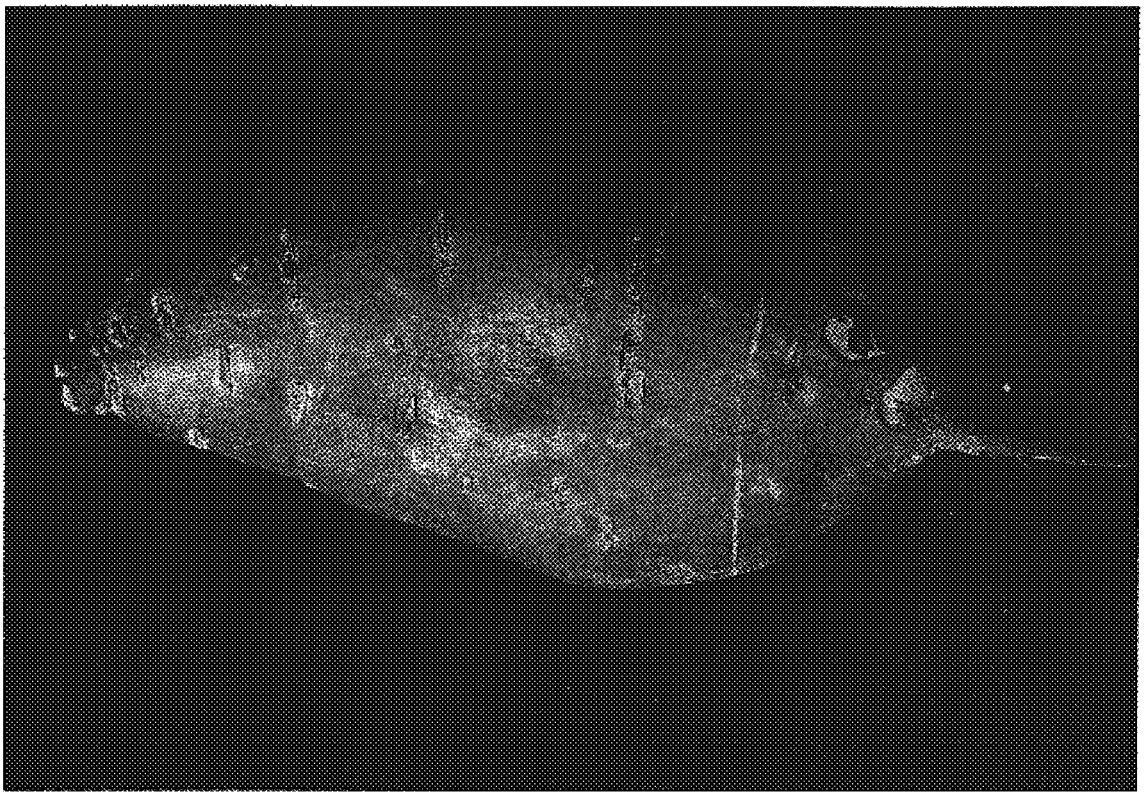
FIG. 1 is a color photograph of the fleshy root form of the novel variety of sweetpotato identified as 'Murasaki-29'.
Figure 2:
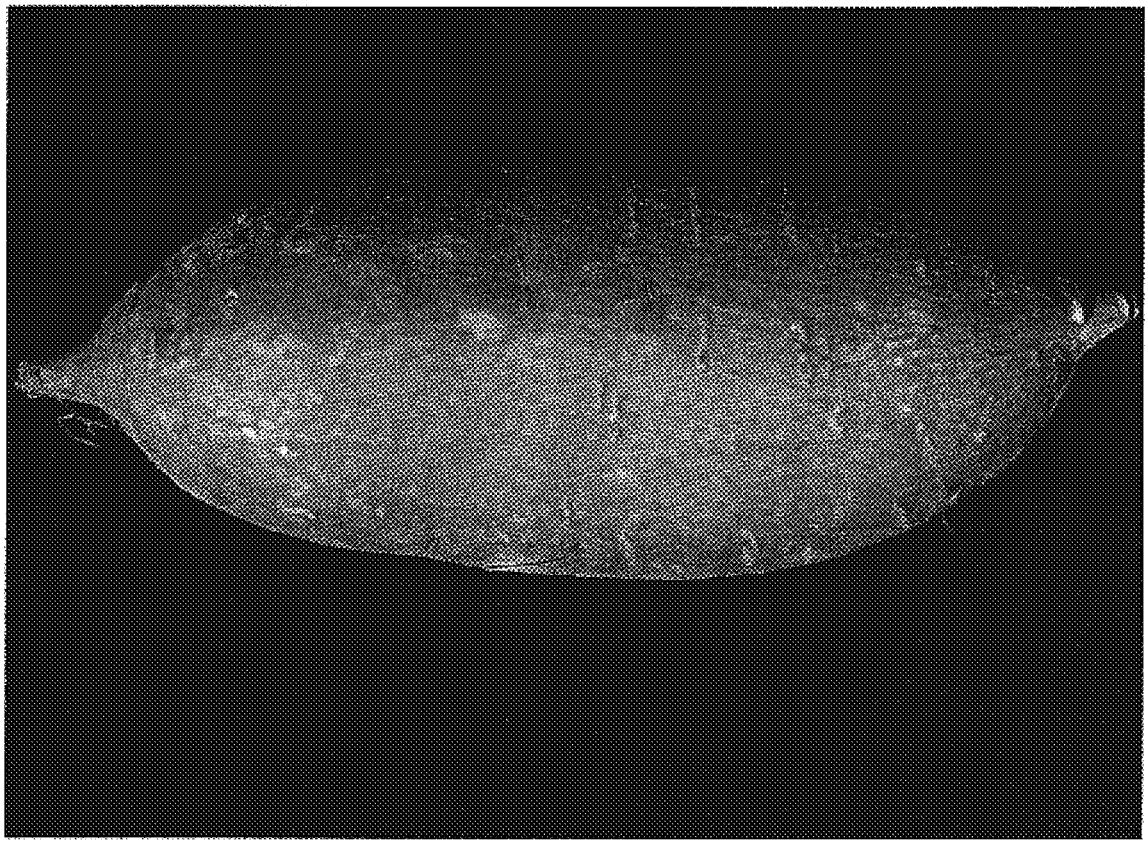
FIG. 2 is a color photograph of the fleshy root form of the sweetpotato variety identified as 'Beauregard'.
Figure 3:
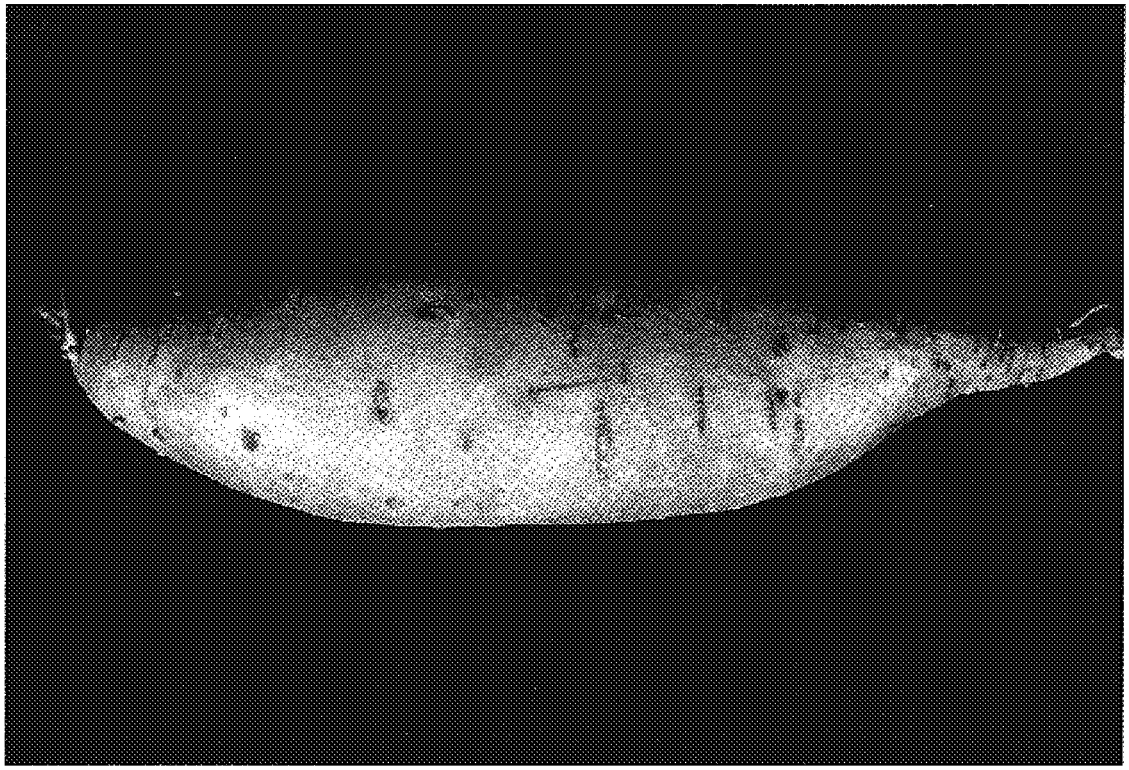
FIG. 3 is a color photograph of the fleshy root form of the sweetpotato variety identified as 'O'Henry'.

FIG. 1 depicts the fleshy root form of the 'Murasaki-29' sweetpotato. The skins vary in color from medium to dark purple both at harvest and after several months of storage, as shown in Table 1. Munsell® Book of Color values for skin and flesh for 'Murasaki-29', 'Beauregard', and 'O'Henry' storage roots at harvest are shown in Table 1. 'O'Henry' had streaks of orange in the flesh, while 'Murasaki-29' has not such streaks. A 'Beauregard' sweetpotato is depicted in FIG. 2 and an 'O'Henry' sweetpotato is depicted in FIG. 3. The skins on 'Murasaki-29' and 'Beauregard' were smooth, while the skin on 'O'Henry' had slight grooves and shallow-set eyes or indentations. 'Murasaki-29' storage roots were elliptical without lobing, and they were shorter than 'Beauregard' storage roots. 'Murasaki-29' cortexes were approximately 5 mm in depth.

TABLE 1

| Variable | Variety | Color |
|---|---|---|
| Skin | 'Murasaki-29' | 7.5 R (red) P (purple) 3/8 |
| | 'O'Henry' | 2.5 Y (yellow) 8/6 |
| | 'Beauregard' | 7.5 R (red) 5/6 |
| Flesh | 'Murasaki-29' | 7.5 Y (yellow) 9/4 |
| | 'O'Henry' | 5 Y (yellow) 9/4 |
| | 'Beauregard' | 2.5 Y (yellow) R (red) 7/10 |

Figure 4:
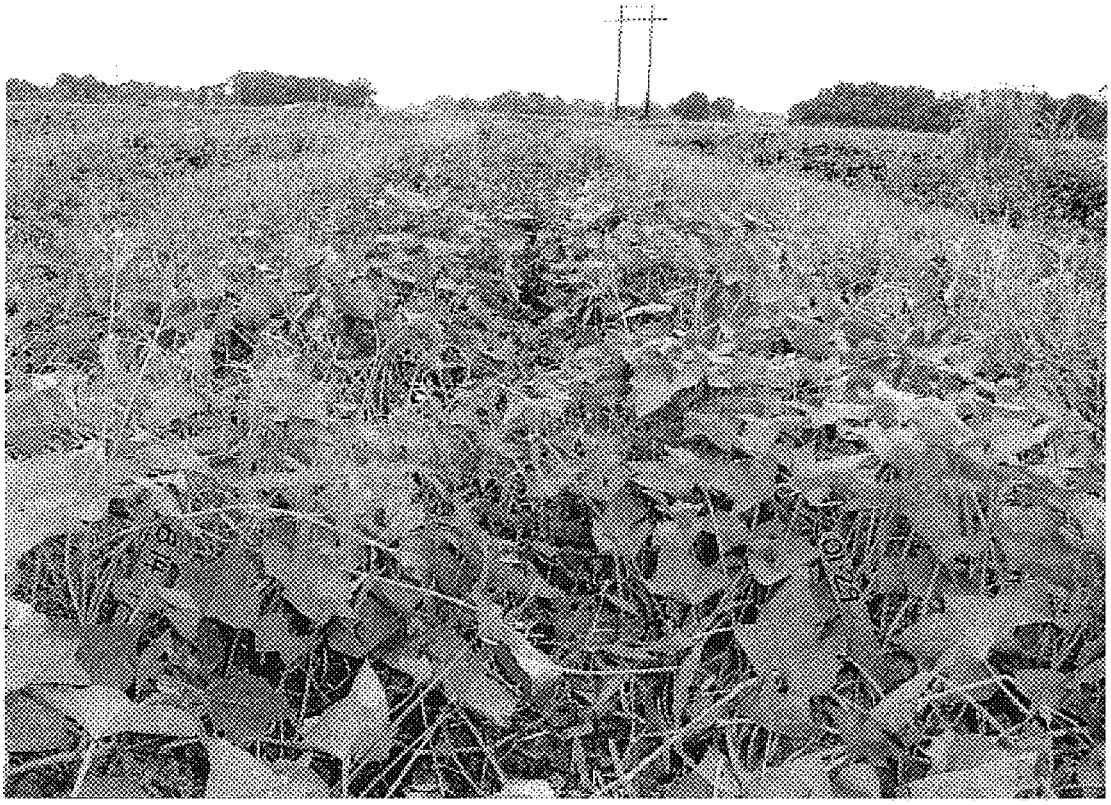
FIG. 4 is a color photograph of the canopy biomasses of the variety of sweetpotato identified as 'Beauregard' (shown on the left side of the photograph) and the novel variety identified as 'Murasaki-29' (shown on the right side of the photograph).

FIG. 4 depicts the canopy biomass of both 'Murasaki-29' sweetpotatoes and 'Beauregard' sweetpotatoes. 'Murasaki-29' had green-stemmed vines [7.5G (green) Y (yellow) (5/6)] from the apex to near the crown of the roots; they darkened to purple [5 R (red) P (purple) (3/6)] near the soil surface. The 'Murasaki-29' canopy biomass appeared to be similar to that for 'Beauregard.' The 'Murasaki-29' canopy architecture was prostrate (28 cm in height from the soil surface) and erect prior to spreading (200 cm radius); 'Beauregard' exhibited a similar prostrate growth habit (25 cm in height from the soil surface). 'O'Henry' exhibited a canopy similar to that seen for 'Beauregard.' 'Murasaki-29' plants exhibited five to six main vines that arose from the main stem near the soil surface. The stem giving rise to these vines typically was about 1.4 cm in diameter; the lateral vines typically were about 150–200 cm in length with diameters of about 0.4–0.5 cm at 65 cm from the base. The base of the vines had diameters of about 0.6 cm, and at the first internode of the first fully-developed leaf from the apex the vines had diameters of about 0.4–0.5 cm. Three to five lateral branches arose from each of the main vines. At the first internode from the apex, the internode length was about 2.1 cm between the first and second fully-developed leaves. Internode lengths for other sections of the vine averaged about 5–6 cm. Unfolded immature leaves were purple [5R (red) P(purple) (3/6)] along the margin and outer leaf lamina before fading by the fifth or sixth open leaf from the apex. Leaf color of the upper surface [7.5 G (green) Y (yellow) (5/6)] and the lower surface [5 G (green) Y (yellow) (6/6)] of the leaves changed little as they matured. Mature leaves at five nodes from the apex had an acute apex, a mostly cordate base, and a smooth leaf margin. Mature leaves were about 12 cm long and about 11 cm wide. Abaxial and adaxial veins were green and similar to the lamina color. Abaxial veins in immature leaves were slightly purple [5 G (green) Y (yellow) (4/4)], which faded as leaves matured. The petiole was green [7.5 G (green) Y (yellow) (5/6)] at its junction with the leaf and remained that color until reaching the nodal junction. A slight groove existed along the length of the petiole (adaxial side), and two very thin, purple [5 R (red) P (purple) 3/6] bands highlighted each half of the petiole, fading to green at the nodal junction. The petiole was about 11 cm long at five nodes from the apex, and about 3.6 mm in diameter at 5 cm from the leaf junction. The dormant nodal meristem was dark green [7.5 G (green) Y (yellow) (5/4)]. Mature leaves of 'Beauregard' and 'O'Henry' were darker [7.5 G (green) Y (yellow) (4/4)] in comparison to 'Murasaki-29' and exhibited purple [5 R (red) P (purple) 4/4] spot at the junction of the petiole and leaf.

A typical inflorescence of 'Murasaki-29' displayed four flowers per peduncle. Peduncles were green [7.5 G (green) Y (yellow) (5/6)], about 12–15 cm long, and about 3.5 mm in diameter. Individual flowers were about 4 cm long from the base of the calyx. The fused flower petals formed a pentagonal pattern with smooth edges. The inner throat of the corolla appeared purple [7.5 P (purple) (5/8)]. The inner and outer limbs of the corolla (outermost area, distal from the calyx) were very light purple [7.5 P (purple) (9/2)]. The five sepals comprising the calyx were elliptic with a cordate apex and appeared green [2.5 G (green) Y (yellow) (7/6)]; three of these sepals were about 12 mm long and about 3.6 mm wide. Two other sepals (interspersed) were about 11–12 mm long and about 2 mm wide. Sepal margins were smooth. Stigmata were about 1.5 to 18 cm long and appeared to be purple [7.5 P (purple) (5/8)]. Five stamens, which were mostly inferior to stigmata, were attached to the ovary. No fragrance was present.

Example 1

Tests Conducted

To confirm that 'Murasaki-29' was a new variety, controlled tests (e.g., pathogen responses and yield) were conducted at the Louisiana Agricultural Experiment Station. 'Beauregard' was selected for comparison because of its dominance in commercial United States sweetpotato acreage. Diseases that commonly affect the growth of sweetpotatoes were selected to test for pathogen responses in both varieties. Scions of 'Murasaki-29' and 'Beauregard' reacted similarly to most diseases evaluated in the controlled tests. 'Murasaki-29' and 'Beauregard' were intermediate to resistance for soil rot caused by *Streptomyces ipomoeae* (Person & W. J. Martin) Waksman & Henrici. 'Murasaki-29' and 'Beauregard' showed similar resistance to Fusarium wilt and to stem rot caused by *Fusarium oxysporum* Schlect. f. sp *batatas* (Wollenw.) Snyd. & Hans.

Nematode reproduction was measured in greenhouse tests. 'Murasaki-29' was highly resistant to southern root-knot nematode, *Meloidogyne incognita* (Kofoid & White 1919) Chitwood 1949 race 3. 'Beauregard' was less resistant to southern root-knot nematode. 'Murasaki-29' and 'Beauregard' exhibited similar resistance to Fusarium root rot caused by *Fusarium solani* (Sacc.) Mart. emend. Snyd. & Hans. 'Murasaki-29' storage roots were more resistant to bacterial soft rot, caused by *Erwinia chrysanthemi* Burkholder, McFadden & Dimock, than 'Beauregard'. 'Murasaki-29' and 'Beauregard' both were resistant to *Rhizopus* soft rot caused by *Rhizopus stolonifer* (Ehr. ex. Fr.) Lind. Incidences of circular spot caused by *Sclerotium rolfsii* Sacc. for 'Murasaki-29' were low (0–3%), similar to that observed for 'Beauregard' (0–5%).

'Murasaki-29' did not appear to show any novel insect resistance. Both 'Murasaki-29' and 'Beauregard' showed similar levels of susceptibility to insect pests, for example, banded cucumber beetles (*Diabrotica balteata* LeConte), and white grubs (*Plectris aliena* Chapin or *Phyllophaga* spp.).

To determine yield production, complete-block trials, using three to four replications of 'Murasaki-29' and 'Beauregard' each, were conducted at various location in Louisiana. There were two to four trials each year over a three-year period. These trials covered a wide range of planting dates and growing days. Average yields were measured for the following grades of roots: U.S. #1 (51–89 mm in diameter, 76–229 mm long); Canner (25–51 mm in diameter, 51–178 mm long); and Jumbo (larger than U.S. #1 in diameter, length, or both, and without objectionable defects). A typical marketable root of 'Murasaki-29' was 60–70 mm in diameter and 140–150 mm long, with mostly round-to-elliptical shapes. The base or distal end tended to be more elongated in comparison to slightly rounder apex (proximal end). U.S. #1 roots typically weighed 200–220 g.

Yield and grade of 'Murasaki-29' were typically less than that of 'Beauregard' (Table 2) in Louisiana, and 'Murasaki-29' did not perform well when planted late. However, white flesh varieties tend to receive a higher market price than conventional dessert types. The difference in the yields of the 'Beauregard' and 'Murasaki-29' were statistically significant ($p \leqq 0.05$) in 2 of 18 trials. In those two instances, 'Beauregard' produced greater yields. These results showed reasonable productivity for a specialty type. 'Murasaki-29' would not directly compete with the dessert type 'Beauregard' in the marketplace, but 'Murasaki-29' compared favorably to 'O'Henry' or 'Kotobuki,' other white flesh sweetpotato varieties. In addition, neither 'O'Henry' nor 'Kotobuki' exhibited good pest or disease resistance. 'Murasaki-29' represented an alternative or adjunct to 'Kotobuki' and 'O'Henry'; 'Murasaki-29' should prove valuable to growers because of its disease resistance characteristics and attractive purple skin.

Average yields of 'Murasaki-29' and 'Beauregard' during a three year period measured as Metric Tons per Hectare ("$MT \cdot ha^{-1}$), are shown in Table 2.

TABLE 2

| | Avg. yield ($Mt \cdot ha^{-1}$)[z] | | | |
|---|---|---|---|---|
| Cultivar | U.S. #1 | Canner | Jumbo | Total marketable |
| Murasaki-29 | 11.8 | 9.8 | 1.1 | 22.7 |
| Beauregard | 17.4 | 9.6 | 7.2 | 34.2 |
| Murasaki-29 | 17.0 | 5.8 | 2.5 | 25.2 |
| Beauregard | 17.1 | 7.7 | 13.9 | 38.7 |
| Murasaki-29 | 12.9 | 5.0 | 9.2 | 27.1 |
| Beauregard | 16.2 | 12.9 | 16.5 | 45.6 |

[z]Averages of 5 trials during 3 years.

'Murasaki-29' should be a valuable commercial specialty sweetpotato variety. 'Murasaki-29' produced plans (sprouts) early and its growth was prolific, when compared to 'Beauregard.' 'Murasaki-29' generally needed more time to harvest (1 to 2 weeks), particularly when planted late. 'Murasaki-29' exhibited greater variability in shape (round to elliptical) than 'Beauregard,' which appeared to depend on soil types and growing environment. Growth cracks also appeared in some plots and reduced the marketable grade.

'Murasaki-29' had good culinary characteristics. It did not require any additional baking time in comparison to dessert-type cultivars. It was characterized as slightly sweet with a somewhat flaky texture and a higher dry matter (30–32%) in comparison to 'Beauregard' and 'O'Henry' (both of which had about 21%–23% dry matter). 'Murasaki-29' was ideally suited for production on land infested with southern root-knot nematode and soil rot.

We claim:

1. A new and distinct variety of *Iponoea batatas* plant named 'Murasaki-29' as described and illustrated in the specification herein.

* * * * *